US 8,734,807 B1

(12) United States Patent
Langlois-Rahme

(10) Patent No.: US 8,734,807 B1
(45) Date of Patent: May 27, 2014

(54) **PREVENTING AND CURING *SCHISTOSOMIASIS MANSONI* BY INHIBITING TRK RECEPTORS ON FEMALE *SCHISTOSOMA***

(71) Applicant: Gabriel Langlois-Rahme, Ottawa (CA)

(72) Inventor: Gabriel Langlois-Rahme, Ottawa (CA)

( * ) Notice: Subject to any disclaimer, the term of this patent is extended or adjusted under 35 U.S.C. 154(b) by 0 days.

(21) Appl. No.: 13/858,016

(22) Filed: Apr. 6, 2013

(51) Int. Cl.
*A01N 63/00* (2006.01)
*A61K 39/00* (2006.01)
*A61K 39/02* (2006.01)
*A61K 39/38* (2006.01)

(52) U.S. Cl.
USPC ...... 424/200.1; 424/50; 424/93.4; 424/184.1; 424/185.1; 424/265.1; 424/269.1; 424/278.1; 424/408; 424/410; 424/439; 435/6.15; 435/7.22; 514/2.3; 514/2.4; 514/4.6; 530/388.6

(58) Field of Classification Search
None
See application file for complete search history.

(56) References Cited

U.S. PATENT DOCUMENTS

| | | | |
|---|---|---|---|
| 5,597,570 A | 1/1997 | Sondermeyer et al. | |
| 2005/0271643 A1 * | 12/2005 | Sorokulova et al. | 424/93.462 |
| 2007/0116826 A1 * | 5/2007 | Prakash et al. | 426/548 |
| 2011/0172445 A1 | 7/2011 | Wataya et al. | |

FOREIGN PATENT DOCUMENTS

| | | |
|---|---|---|
| EP | 0318879 A1 | 6/1989 |
| WO | WO/83/00929 A1 | 3/1983 |
| WO | WO/83/01837 A1 | 5/1983 |
| WO | WO/94/06903 A1 | 3/1994 |
| WO | WO/97/11191 A1 | 3/1997 |
| WO | WO/97/33610 A1 | 9/1997 |
| WO | WO/98-06734 A1 | 2/1998 |
| WO | WO/00/17654 A1 | 3/2000 |
| WO | WO/00/32804 A1 | 6/2000 |
| WO | WO/02/05821 A1 | 1/2002 |
| WO | WO/02/066646 A2 | 8/2002 |
| WO | WO/03/02597 A2 | 1/2003 |
| WO | WO 03/063785 * | 8/2003 |
| WO | WO/2004/043998 A1 | 5/2004 |
| WO | WO/2004/067698 A2 | 8/2004 |
| WO | WO/2005/023979 A2 | 3/2005 |
| WO | WO/2006/088951 A2 | 8/2006 |
| WO | WO/2007/014415 A1 | 2/2007 |
| WO | WO/2007/118292 A2 | 10/2007 |
| WO | WO/2008/003007 A2 | 1/2008 |
| WO | WO/2011/033290 A2 | 3/2011 |
| WO | WO/2012/138377 A2 | 10/2012 |
| WO | WO/2012/145398 A1 | 10/2012 |

OTHER PUBLICATIONS

Knobloch et al., (Int. J Parasitol. 2006. vol. 36(12): 1261-72).*
Li et al., Parasitol. Res. 2009. 105:1643-1651.*
Wynn Hyperlink TA, Cheeverhyperlink AW, Jankovichyperlink D, et al. An IL-12-based vaccination method for preventing fibrosis induced by *Schistosome infection*. 1995, 594-596, 376(6541), Nature, National Institute of Allergy and Infectious Diseases, National Institutes of Health, Bethesda, MD 20892. Publisher: London, Macmillan Journals ltd, London, England.
El Kouni MH. Efficacy of combination therapy with tubercidin and nitrobenzylthioinosine 5'-monophosphate against chronic and advanced stages of schistosomiasis. 1991, 815-820, 41(5). Biochem Pharmacology, Providence, RI 02912, USA.
Dovey HF, McKerrow JH, Wang CC. Action of tubercidin and other adenosine analogs on *Schistosoma mansoni* schistosomules. Mol 1985, 185-198, 16(2), Biochem Parasitol., Publisher: Elsevier/North-Holland Biomedical Press, Amsterdam, Netherlands.
Doenhoff MJ, Pearson S, Dunne D et al. Immunological control of hepatotoxicity and parasite egg excretion in *Schistosoma mansoni* infections: stage specificity of the reactivity of immune serum in T-cell deprived mice. 1981, 41-53, 75(1), Transactions of the Royal Society of Tropical Medicine and Hygiene. Publisher: Royal Society of Tropical Medicine and Hygiene and Oxford University Press, Oxford, England.
Michaels RM, Pratahyperlink A. Evolution and characteristics of *Schistosoma mansoni* eggs laid in vitro. 1968, 921-930, 54(5), Journal Parasitology, Publisher: Lawrence, Kans. [etc.] American Society of Parasitologists, USA.
Tran MH, Pearson MS, Bethonyhyperlink JM., et al. Tetraspanins on the surface of *Schistosoma mansoni* are protective antigens against schistosomiasis. Nat Med. 2006, 835, 840, 812(7), Publisher: Nature Publishing Company, New York, USA.

* cited by examiner

Primary Examiner — Ja'Na Hines

(57) ABSTRACT

*Schistosomiasis mansoni* is caused by flukes called *Schistosoma(es)* that enters the human body through the skin in *Schistosoma* infested waters. The *Schistosomes* travel from the skin into human blood vessels where they mate, produce antigen containing eggs that travel from the blood vessels into the small intestines, where they are released in the human feces. Male and female *Schistosome* mates in human blood vessels, male *Schistosomes* secrete a protein called TGR β protein to the Trk receptor sites on the females *Schistosomes* membranes. The process stimulates the formation of chemical SmInAct in female *Schistosomes*, a chemical necessary for the female *Schistosomes* to produce eggs. This novel technique describes new methods to inhibit Trk receptor sites on female *Schistosome* membranes using Trk inhibitor agent to prevent TGR β proteins from binding to the Trk receptor sites. Thus, preventing SmInAct from being created in female *Schistosomes*, preventing production of eggs and *Schistosomiasis*.

12 Claims, No Drawings

PREVENTING AND CURING *SCHISTOSOMIASIS MANSONI* BY INHIBITING TRK RECEPTORS ON FEMALE *SCHISTOSOMA*

BACKGROUND OF THE INVENTION

Transforming growth factor beta signaling is recognized for its essential role in embryogenesis in deuterostomes and arthropod protostomes. The tropical disease *Schistoromiasis* is caused by the metazoan parasite *Schistosomes*, classified by the lophotrochozoan phylum Platyhelminthes. Activation of the TGF-beta signaling in metazoans begins at the cell surface when a dimeric ligand binds to a complex composed of types 1 and 2 serine/theorine kinase receptors. Due to ligand binding, type 2 serine/theorine kinase receptors phosphorylates (gives a phosphate group from a high energy molecule such as ATP) type 1 serine/theorine kinase receptor site, activating it, and causes it to phosphorylate cytoplasmic Smad protein, which translocates to the nucleus and mediates gene expression. Components of a functional TGF-β pathway (s) includes one type I receptor, *Schistosoma mansoni* receptor kinase-1 known as SmRK1, *Schistosoma. mansoni* transforming growth factor-β type I receptor known as SmTβ RI, one type II receptor known as SmRK2 and SmTβ RII, and three Smads, have been identified in *Schistosoma. mansoni*, with components localized to either the surface of the fluke or reproductive tissues of the female fluke.

The male and female *Schistosomes* enter the human blood vessels by cutting its way through the outside layer of the human skin, where the flukes feed on hemoglobin. Sexual production later occurs within the mesenteric vasculature, where the female fluke produces approximately 300 eggs per day. Development of an immature egg to a mature egg that contains a miracidum takes approximately 5 days. The egg travels from the veins into the small intestines, and through the digestive path with the intestines to be released within the feces into the external environment. Many of the eggs do not reach external environment as they become trapped within the host tissues causing an immune response to the egg antigens, and some are swept into the liver where they cause granulomas on the liver, obstructing the portal veins and causing enlargement of the liver.

TGF-beta homologue SmInAct is necessary for the formation of *Schistosomiasis monsani* as shown in RNA interference studies indicating that infertile *Schistosomes* have a deficit of SmInAct protein. The formation of SmInAct is controlled by TGF-beta signalling, where the initiation of the mediation of the gene is caused by the release of TGR beta protein from the male *Schistosome* onto the serine/theorine receptor site 2 on the female *Schistosome*.

An inhibitor or antagonist represses and prevents another molecule from engaging in a reaction through blocking the pathway necessary for the reaction, such as physically blocking the pathway necessary for a molecule to reach a receptor site. Trk receptor sites are serine/theorine kinase receptors found on female *Schistosomes* necessary for the TGF-beta signaling caused by TGR beta protein for the formation of SmInAct. Inhibitor Trk receptor agents act as inhibitors or antagonist that prevent TGR beta protein from reacting to Trk receptor sites. Due to the numerous Inhibitor Trk receptor agents, solely the Trk inhibitor Decorin will be focused on within the introduction. Decorin is coded by the DCN gene found within the human genome. (Decorin, a ubiquitous small cellular or pericellular matrix proteoglycan, belongs to the small leucine-rich proteoglycan (SLRP) family and consists of a core protein and a covalently linked glycosaminoglycan chain of either chondroitin sulfate or dermatan sulfate. Decorin is a component of connective tissue that interacts with several extracellular matrix components, such as type I collagen and fibronectin, and plays a role in matrix assembly. Decorin core protein also binds to growth factors such as TGF-beta, and the decorin endocytosis receptor. Decorin can suppress the growth and the metastasis of a wide range of cancer cells in vitro by attenuation of the EGFR-mediated intacellular signaling and induction of apoptosis. Decorin can be found within the human urine, where surplus production of Decorin is released within the human urine, assuring the safety of the use of Trk receptor site Decorin as the body naturally releases the overproduction of decorin through the urinary system.

Several Inhibitor Trk receptor agents correspond to DNA sequences within the genome of living organisms for natural production of the inhibitor. The corresponding DNA sequence can be obtained through placing the cell of an organism within a solution containing lysosomes and SDS buffers, then centrifuging the solution within the corresponding machine and precipitating the DNA with cold ethanol. The corresponding DNA sequence can then be located using several methods, including but not restricted to Southern blotting with radioisotope probes that anneal to the nucleic acids of the corresponding DNA sequence. The DNA sequence can then be removed by digesting the DNA with the corresponding restriction enzymes. Once the DNA sequence possessing the gene for production of Inhibitor Trk receptor agents is obtained, it can be placed in several organisms such as rice plants or probiotic bacteria. The biolostic method can be used to insert DNA within the genome of rice plants, resulting in Inhibitor Trk receptor agents within the rice grown from the plant. Probiotic bacterial lives within the human body in mutualism due to the bacteria's beneficial effect to humans. Bacteria holds ring shaped plasmids with the ability of carrying genetic information in and out of the bacteria. Using the restriction enzymes used to cleave DNA sequence, one can cleave the plasmid and insert the Inhibitor Trk receptor agent gene within the plasmid with DNA ligase. Several methods can then be used to insert the plasmid into its corresponding pro-bacteria (or probacteria), genetically modifying the pro-bacteria into allowing the bacteria to produce Inhibitor Trk receptor agents. Selecting probiotic bacteria that lives near the mesontatic veins will allow the formation of Inhibitor Trk receptor agents, inhibiting female *Schistosomes* from producing eggs.

BRIEF SUMMARY OF THE INVENTION

*Schistosomiasis mansoni* is a major neglected tropical disease that has affected more than 200 million people worldwide and is responsible for hundreds of thousands of deaths annually. The disease is caused by flukes called *Schistosoma* or *Schistosome(s)* that enters the human body through the skin in *Schistosoma(e)* infested waters. The *Schistosomes* travel from the skin into human blood vessels where they mate, and produce eggs that then travel from the blood vessels into the small intestines, where they are released in the human feces. However, over 50% of the *Schistosome* eggs fail to reach external environment and become trapped in the human host tissue, causing an immune response against the toxic egg antigens. Here, we describe a novel method of preventing the disease *Schistosomiasis* by preventing formation of eggs in female *Schistosomes* that are needed to instigate the disease *Schistosomiasis*. When a male and female *Schistosome* mates in human blood vessels, male *Schistosomes* secrete a protein called TGR β protein to the Trk receptor sites on the females

*Schistosomes* membranes. The process stimulates the formation of chemical SmInAct in female *Schistosomes*, a chemical necessary for the female *Schistosomes* to produce eggs. In this novel technique, Trk receptor sites on female *Schistosome* membranes will be inhibited using a Trk inhibitor agent (such as Decorin; ANA 12, TrkB receptor antagonist.) or a Trk inhibitor agent (such as AG 879, TrkA inhibitor; GW 441756, selective TrkA inhibitor; Lestaurtinib, TrkA inhibitor; Ro 08-2750, TrkA inhibitor.) in order to prevent TGR β proteins from binding to the Trk receptor sites. The result of no stimulation caused by TGR β proteins at the Trk receptor sites will prevent SmInAct from being created in female *Schistosomes*, thus preventing female *Schistosomes* from producing *Schistosome* eggs. As a result, no antigen containing *Schistosome* eggs will be trapped in the human hosts' tissue, and *Schistosomiasis mansoni* will not occur.

BRIEF DESCRIPTION OF DRAWING (None)

DETAILED DESCRIPTION OF THE INVENTION

The claims for the present invention were presented in a simple and clear steps in order to disclose new methods for preventing the occurrence, recurrence and the progression of *Schistosomiasis mansoni* disease. The methods of the claims describing new techniques to prevent the formation of SmInAct in female *Schistosomes*, a protein necessary for the embryological development of antigen containing *Schistosome* eggs. The female *Schistosome* will be impaired of SmInAct through placing inhibitor Trk agents in contact with the female *Schistostomes* by using methods of the 3 independents claims or by applying the dependents methods via ways of life styles in order to inhibit the Trk receptor sites. The inhibitor/antagonist agent will inhibit the serine/theorine kinase receptor site 2 on the female *Schistosome*, preventing phosphorylation of serine/therine kinase receptor site 1, preventing phosphorylation of cytoplasmic Smad protein, preventing mediation and activation of the gene necessary for the formation of SmInAct. The inhibition of the Trk receptor sites of the female *Schistosomes* will thus render the female *Schistosome* infertile, resulting in no antigen containing eggs trapped within human tissues. Therefore it will preventing the occurrence and the recurrence of *Schistosomiasis mansoni* disease.

The dependent claims are describing the use of Decorin which can be found within the human urine, where surplus production of Decorin is released within the human urine, assuring the safety of the use of Trk receptor site Decorin as the body naturally releases the overproduction or of decorin through the urinary system.

Other Inhibitor Trk receptor agents correspond to DNA sequences within the genome of living organisms for natural production of the inhibitor. The corresponding DNA sequence can be obtained through placing the cell of an organism within a solution containing lysosomes and SDS buffers, then centrifuging the solution within the corresponding machine and precipitating the DNA with cold ethanol. The corresponding DNA sequence can then be located using several methods, including but not restricted to Southern blotting with radioisotope probes that anneal to the nucleic acids of the corresponding DNA sequence. The DNA sequence can then be removed by digesting the DNA with the corresponding restriction enzymes. Once the DNA sequence possessing the gene for production of Inhibitor Trk receptor agents is obtained, it can be placed in several organisms such as rice plants or probiotic bacteria. The biolostic method can be used to insert DNA within the genome of rice plants, resulting in Inhibitor Trk receptor agents within the rice grown from the plant. Probiotic bacterial lives within the human body in mutualism due to the bacteria's beneficial effect to humans. Bacteria holds ring shaped plasmids with the ability of carrying genetic information in and out of the bacteria. Using the restriction enzymes used to cleave DNA sequence, one can cleave the plasmid and insert the Inhibitor Trk receptor agent gene within the plasmid with DNA ligase. Several methods can then be used to insert the plasmid into its corresponding probacteria, genetically modifying the probacteria into allowing the bacteria to produce Inhibitor Trk receptor agents. Selecting probiotic bacteria that lives near the mesontatic veins will allow the formation of Inhibitor Trk receptor agents, inhibiting female *Schistosomes* from producing eggs.

The independent claim 1 is describing a novel method for preventing formation of eggs from female *Schistosomes* in order to treat and prevent the development of the occurrence and the recurrence of a major disease called *Schistosomiasis mansoni* which affects more than 200 million people worldwide and is causing deaths for hundreds of thousands annually. This novel method is disclosing several consequently and related steps by placing cell with corresponding DNA sequence for Trk inhibitor agent within solution containing lysosomes and SDS buffer, centrifuging the solution and precipitating the DNA with cold ethanol, locating corresponding DNA sequence with gene to produce Trk inhibitor agent, removing DNA sequence corresponding to gene by digesting DNA with adequate restriction enzyme, using the same restriction enzyme to cleave plasmid, inserting gene into plasmid using DNA ligase, inserting plasmid into a specific probiotic bacteria that has previously been found within the human small intestine or human bloodstream vessel, and then, administrating (orally) the modified probiotic bacteria to persons at risk that act as a long term inhibitor of Trk receptors found on female *Schistosomes*.

The independent claim 2 is also describing a novel method for preventing formation of eggs from female *Schistosomes* for the same purpose of preventing development, occurrence and recurrence of disease *Schistosomiasis mansoni*. The steps of the method of this claim are described as the following: placing cell with corresponding DNA sequence for Trk inhibitor agent within solution containing lysosomes and SDS buffer. centrifuging the solution and precipitating the DNA with cold ethanol, locating corresponding DNA sequence with gene to produce Trk inhibitor agent, replicating the gene using Polymerase Chain Reaction, placing the gene into tree or plant seed using biolistic method, allowing the modified fruits or vegetables from modified tree or plant to grow the Trk inhibitor agents, offering humans to ingest the modified vegetable, fruit or food related products, and allowing absorption of Trk inhibitor from small intestines to bloodstream vessels. Therefore, the formation of eggs from the female *Schistosomes* will be prevented and par consequently, preventing the occurrence and the recurrence of *Schistosomiasis mansoni* disease will be achieved.

The method of the independent claim 3 is also describing novel steps for preventing the formation of eggs from female *Schistosomes*, by obtaining Trk inhibitor agent, placing the said Trk inhibitor agent into a capsule, and administrating the said capsule orally to human, which will prevent the occurrence, recurrence and development of *Schistosomiasis mansoni* disease.

In addition, the methods of claims 1-3 may possibly cure the patients who are already infected by *Schistosomiasis mansoni* disease. However, this present statement needs further clinical research achievements and follow up the patients for a period of time to assure the complete relief from this disease without the risk of early recurrence.

In general, all disclosed methods, uses and techniques of the 17 dependents claim 4-20) are novel, and beneficial to certain people and communities (who are at risk of developing such major and infected disease, *Schistosomiasis mansoni*) with easy and daily use (ex. developing gums for human mastication) which would be applied to their daily life style without side effect or risks of toxicity. For example, claims 4 and 5, are specifically describing the use of 'Decorin', a Trk inhibitor receptor secreted by the body, instead of a synthetic Trk inhibitor receptor for preventing development of disease *Schistosomiasis mansoni*. Therefore, the use of Decorin will allow nature elimination without significant risk of toxicity related to overdose, defect of metabolism, accumulation or elimination by our human body.

The methods of claims 6 of 17 are also novels and applied to add either one of Trk inhibitor agent capsules, probiotic bacteria or product of genetically modified plant to certain daily meals or drinks to people and communities who are at risk of developing the disease *Schistosomiasis mansoni* from infected water or elsewhere.

The methods disclosed for claim 17-20 are also novel and original to aim the prevention of developing a major disease, *Schistosomiasis mansoni*, to a group of smokers who are already smokers and are classified at risk for developing this disease. Therefore, the smokers who are at risk instead of just smoking cigarette or cigar with all major risks of developing lungs cancer (and many others diseases related to smoking), they could at least be partially beneficial by preventing themselves from *Schistosomiasis mansoni*. Therefore, by smoking a cigar or cigarette which have placed Trk inhibitor agent capsules, probiotic bacteria or product of genetically modified plant within top end tobacco filter foot (either cigar or cigarette), it will produce buccal or sublingual absorption of the Trk inhibitor agent, probiotic bacteria or product of genetically modified plant into the blood, and therefore, prevent them from developing the disease *Schistosomiasis mansoni*.

CONCLUSION

Referring to the methods discussed with the claims section, the instigators necessary for the causation of the disease *Schistosomiasis mansoni* will be rendered harmless and unable to cause the disease. This will be done through preventing the formation of SmInAct in female *Schistosomes*, a protein necessary for the embryological development of antigen containing *Schistosome* eggs. The female *Schistosome* will be impaired of SmInAct through placing inhibitor Trk agents in contact with the female *Schistostomes* using one of the several possible methods showed within the claims. The inhibitor will inhibit the serine/theorine kinase receptor site 2 on the female *Schistosome*, preventing phosphorylation of serine/therine kinase receptor site 1, preventing phosphorylation of cytoplasmic Smad protein, preventing mediation and activation of the gene necessary for the formation of SmInAct. The inhibition of the Trk receptor sites of the female *Schistosomes* will thus render the female *Schistosome* infertile, resulting in no antigen containing eggs trapped within human tissues, preventing the occurrence of *Schistosomiasis mansoni*.

Terminology: Inhibitor Trk receptors' agent means inhibitor or antagonist to Trk receptors. The term Trk inhibiter agent includes Trk Inhibiter such as AG 879 (found within NTrkl gene), GW 441756, AZ 23, Ro 08-2750, CEP-701, Decorin and Trk Antagonist such as Amytriptyline, JCI, BDNF, 7,8-Dihydroxy-2-phenyl-4H-1-benzopyran-4-one.

The invention claimed is:

1. A method for preventing formation of eggs from female *Schistosomes*, the method comprising the steps of: obtaining from a cell a DNA sequence for human Decorin (hDCN), a Tropomyosin-receptor kinase (Trk) inhibitor agent within solution containing lysosomes and SDS buffer, centrifuging the solution and precipitating the DNA with cold ethanol, locating the DNA sequence to produce the hDCN gene, removing the DNA sequence by digesting the DNA with adequate restriction enzyme, using the same restriction enzyme to cleave plasmid, inserting the gene into a plasmid using DNA ligase, inserting the plasmid into a specific probiotic bacteria that is naturally found within a human small intestine or in human blood vessel near small intestine to produce a modified probiotic bacteria, and administrating an effective amount of the modified probiotic bacteria to persons at risk of *Schistosomiasis*, wherein said method prevents the formation of eggs from female *Schistosomes*.

2. A method for preventing formation of eggs from female *Schistosomes*, the method comprising the steps of: obtaining from a cell DNA sequence for human Decorin (hDCN), a Tropomyosin-receptor kinase (Trk) inhibitor agent within solution containing lysosomes and SDS buffer, centrifuging the solution and precipitating the DNA with cold ethanol, locating the DNA sequence with gene to produce the hDCN gene, replicating the gene using Polymerase Chain Reaction, placing the hDCN gene into a fruit and/or vegetable tree and/or plant seed using biolistic method to produce modified fruits and/or vegetables, allowing the modified fruits and/or vegetables to grow the hDCN, offering humans to ingest the modified vegetable, fruit and/or food related products, and allowing absorption of hDCN from small intestines into the bloodstream, wherein said method prevents the formation of eggs from female *Schistosomes*.

3. The method according to claim 1 further comprising the step of placing the modified probiotic bacteria into capsules, rice or cereal flour, salt, spices, ketchup, dressing, dip, sugar, candies or sold baby formula, wherein consumption prevents development of egg formation.

4. The method according to claim 2 further comprising the step of placing the modified fruits and/or vegetables into capsules, rice or cereal flour, salt, spices, ketchup, dressing, dip, sugar, candies or sold baby formula, wherein consumption prevents development of egg formation.

5. The method according to claim 1 further comprising the step of placing the modified probiotic bacteria within bottled water, juice, soft drink, milk, coffee, tea, herbal tea, liquid baby formula or alcohols, wherein consumption prevents development of egg formation.

6. The method according to claim 2 further comprising the step of placing the modified fruits and/or vegetables within bottled water, juice, soft drink, milk, coffee, tea, herbal tea, liquid baby formula or alcohols, wherein consumption prevents development of egg formation.

7. The method according to claim 1 further comprising the step of placing the modified probiotic bacteria within gum or tooth paste formula to produce buccal or sublingual absorption, wherein absorption prevents development of egg formation.

8. The method according to claim 2 further comprising the step of placing the modified fruits and/or vegetables within gum or tooth paste formula to produce buccal or sublingual absorption, wherein absorption prevents development of egg formation.

9. The method according to claim 1 further comprising the steps of placing the modified probiotic bacteria within a cream substance, transdermal drug-eluting patches, baby diapers or lotion wherein applying onto the skin for absorption into the bloodstream to prevent the development of egg formation.

10. The method according to claim 2 further comprising the steps of placing the modified fruits and/or vegetables within a cream substance, transdermal drug-eluting patches, baby diapers or lotion wherein applying onto the skin for absorption into the bloodstream to prevent the development of egg formation.

11. The method according to claim 1 further comprising the steps of placing the modified probiotic bacteria within—a top end tobacco filter wherein smoking produces buccal, sublingual or lips absorption of the modified probiotic bacteria into the bloodstream to prevent the development of egg formation.

12. The method according to claim 2 further comprising the steps of placing the modified fruits and/or vegetables within—a top end tobacco filter wherein smoking produces buccal, sublingual or lips absorption of the modified probiotic bacteria into the bloodstream to prevent the development of egg formation.

* * * * *